United States Patent
Lindenthal et al.

(10) Patent No.: US 9,579,330 B2
(45) Date of Patent: Feb. 28, 2017

(54) USE AND APPLICATION REGIMEN OF A PHARMACEUTICAL COMPOSITION CONTAINING LEVONORGESTREL AND A COX INHIBITOR FOR ON-DEMAND CONTRACEPTION

(71) Applicant: BAYER PHARMA AKTIENGESELLSCHAFT, Berlin (DE)

(72) Inventors: Bernhard Lindenthal, Berlin (DE); Katrin Waellnitz, Berlin (DE); Peter Serno, Bergisch Gladbach (DE); Stefanie Lindemann, Berlin (DE); Ulrike Fuhrmann, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/647,740

(22) PCT Filed: Nov. 19, 2013

(86) PCT No.: PCT/EP2013/074167
§ 371 (c)(1),
(2) Date: May 27, 2015

(87) PCT Pub. No.: WO2014/079840
PCT Pub. Date: May 30, 2014

(65) Prior Publication Data
US 2016/0000805 A1  Jan. 7, 2016

(30) Foreign Application Priority Data

Nov. 22, 2012 (EP) .................... 12193725
Sep. 26, 2013 (EP) .................... 13186133

(51) Int. Cl.
| | | |
|---|---|---|
| *A61K 31/567* | (2006.01) | |
| *A61K 9/20* | (2006.01) | |
| *A61K 31/18* | (2006.01) | |
| *A61K 31/192* | (2006.01) | |
| *A61K 31/196* | (2006.01) | |
| *A61K 31/405* | (2006.01) | |
| *A61K 31/5415* | (2006.01) | |

(52) U.S. Cl.
CPC .............. *A61K 31/567* (2013.01); *A61K 9/20* (2013.01); *A61K 31/18* (2013.01); *A61K 31/192* (2013.01); *A61K 31/196* (2013.01); *A61K 31/405* (2013.01); *A61K 31/5415* (2013.01)

(58) Field of Classification Search
CPC ........ A61K 31/567; A61K 9/20; A61K 31/18; A61K 31/192; A61K 31/196; A61K 31/405; A61K 31/5415
See application file for complete search history.

(56) References Cited

FOREIGN PATENT DOCUMENTS

| | | |
|---|---|---|
| EP | 0 876 815 A1 | 11/1998 |
| WO | 03/045397 A1 | 6/2003 |
| WO | 03/051338 A1 | 6/2003 |
| WO | 2007/045513 A1 | 4/2007 |
| WO | 2010/119029 A1 | 10/2010 |
| WO | 2010/119030 A1 | 10/2010 |
| WO | 2010/149273 A1 | 12/2010 |

OTHER PUBLICATIONS

Aitken et al., "Bridging the gap between male and female fertility control; contraception-on-demand," Contraception, 2008, 78:S28-S35.
Eskin et al, "In Vitro Responses of the Spermatozoa-Cervical Mucus System Treated with Prostaglandin (F 2a)," Obstetrics and Gynecology, 1973-436-439.
Jonsson et al., "Autonomic nervous modulation and effects of a prostaglandin synthase inhibitor on human cervical secretion," Human Reproduction, 1993, 8(8):1168-1172.
Massai et al., "Does meloxicam increase the incidence of anovulation induced by single administration of levonorgestrel in emergency contraception? A pilot study," Human Reproduction, 2007, 22(2):434-439.
Smith et al., "Reversible Ovulatory Failure Associated With the Development of Luteinized Unruptured Follicles in Women with Inflammatory Arthritis Taking Non-Steroidal Anti-Inflammatory Drugs," British Journal of Rheumatology, 1996, 35:458-462.
von Hertzen et al., "Efficacy and Side Effects of Immediate Postcoital Levonorgestrel Used Repeatedly for Contraception," WHO, Contraception, 2000, 61:303-308.

*Primary Examiner* — Sahar Javanmard
(74) *Attorney, Agent, or Firm* — Resek Liang & Frank LLP; Stanley D. Liang

(57) ABSTRACT

The invention relates to a method of hormonal female controlled "on demand" contraception, in which a pharmaceutical preparation comprising a COX inhibitor and levonorgestrel is taken on demand prior to expected sexual intercourse. Further subjects of the invention relate to pharmaceutical compositions and application regimes for "on demand" contraception.

17 Claims, 1 Drawing Sheet

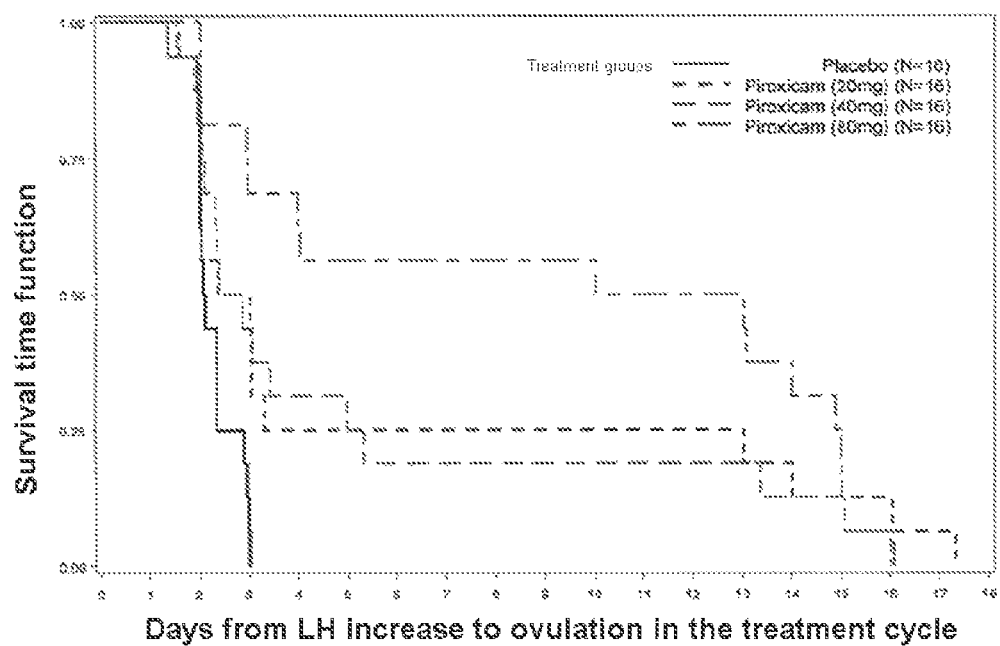

USE AND APPLICATION REGIMEN OF A PHARMACEUTICAL COMPOSITION CONTAINING LEVONORGESTREL AND A COX INHIBITOR FOR ON-DEMAND CONTRACEPTION

The present invention relates to the subject matter characterized in the patent claims, i.e.
(a) a method of female controlled "on demand" contraception, in which a pharmaceutical preparation comprising levonorgestrel (LNG) and a COX inhibitor selected from the group of indomethacin, diclofenac, naproxen, ibuprofen, nimesulide, ketoprofen, meloxicam, piroxicam is administered on demand in a period of up to 24, preferably in a period of 0-12, hours prior to sexual intercourse and
(b) the use of a pharmaceutical preparation comprising, as active ingredients, levonorgestrel and a COX inhibitor, in particular diclofenac, piroxicam, naproxen, ibuprofen or indomethacin for "on demand" contraception, in which the pharmaceutical preparation is administered on demand and once prior to expected sexual intercourse.

Alternatively, the pharmaceutical preparation used in the method can also consist of 2 tablets, the first being taken prior to sexual intercourse and the second being taken directly after sexual intercourse.

The invention further provides an application regime for "on demand" contraception, in which an oral pharmaceutical composition comprising a COX inhibitor and levonorgestrel is taken in a dose of 50-500 µg in a period of 0-12 hours prior to sexual intercourse, followed by a further oral pharmaceutical composition comprising 500 to 1500 µg LNG and optionally a COX inhibitor in a period of up to 48 hours after sexual intercourse.

The invention further provides a kit for "on demand" contraception comprising two pharmaceutical preparations to be administered orally, in which the first preparation comprises a COX inhibitor and low dose LNG in a dose of 50-500 µg and the second preparation comprises "high dose" LNG in a dose of 500-1500 µg, where the second preparation can optionally additionally likewise comprise a COX inhibitor. Suitable COX inhibitors are the aforementioned COX inhibitors.

Hormonal contraception with daily orally administered low dosages of synthetic gestagens and estrogens is, alongside the administration of a gestagen by means of an intrauterine system (IUS), such as e.g. Mirena®, currently the method which has shown the best effectiveness in preventing pregnancies in clinical studies.

Oral contraception requires a continuous, daily taking of hormone-based pills, irrespective of the frequency of sexual intercourse and thus the need for contraceptive protection.

For women having irregular or infrequent sexual intercourse, this therefore results in an unnecessarily high and long exposure to hormones. Specifically for this group of users there is therefore the need for a preparation which can be taken only as required and close to the time before, and optionally also directly after, sexual intercourse, but at the same time offers similarly high (contraceptive) protection to the classic oral contraceptives.

Although there has been such a need for decades (Canzler et al, Zbl. Gynäkol, 1984, 106:1182-1191), there has hitherto been no preparation which permits an "on demand"[1] contraceptive (Aitken et al, Contraception, 2008, 78: p. 28-p 35).

[1] For on demand contraception, the literature also uses the terms contraception on demand, precoital contraception, pericoital contraception as synonyms.

Alternatively, women therefore often resort to products which have actually been tested and approved for emergency contraception or other uses. Mention is to be made here in particular of a pill in which 1.5 mg of levonorgestrel is taken as a single dose within 72 hours after coitus. This preparation is known e.g. under the trade name Postinor®, Plan B® or Levonelle® and is described e.g. in EP 1448207.

A study carried out in 2003 in Ghana reports that women use norethisterone tablets, which are approved for treating various gynaecological disorders, as "on demand" contraceptive.

Anecdotal reports and data collected by Family Health International confirmed that women in many countries, especially developing countries, in South America and Africa, but also in countries such as Great Britain intentionally use preparations developed for emergency contraception also for "on demand" contraception.

In doing so, however, the fact is overlooked that the administered dose of 1.5 mg of levonorgestrel, despite general good tolerability, is very high. For example, this amount corresponds to one dose as is otherwise taken spread over a period of 2 months when regularly taking a hormone-containing pill (such as e.g. Microgynon®). If such a pill intended for emergency contraception is indeed used several times within a month, the monthly hormone dose can easily lead to a 10-fold higher hormone load than would be reached upon regularly taking an oral contraceptive.

Such a high dose is justifiable for a single application as is required for emergency contraception, but less advantageous for an "on demand" situation, which may also occur several times within the month. Thus, although on account of the generally good tolerability of LNG, even when a high dose is taken several times, no serious side effects are to be expected, such a multiple dose does have effects on the cycle of the user, which becomes considerably disrupted.

Moreover, in the event of the off-label use of preparations for emergency contraception as "on demand" contraception, the users overlook the fact that these preparations do not offer anywhere near the same contraceptive safety[2] as a regularly taken, hormone-containing oral contraceptive.

[2] Raymond et al. Obstet Gynecol 2011; 117:673-81

WO 2010/119030 describes an "on demand" preparation in which, as gestagen, levonorgestrel or norgestrel are used in a dose range from 0.5 to 1.5 mg, where the preparation should be used 24 hours prior to sexual intercourse. However, since this product is fundamentally identical to the available products for emergency contraception, this product also does not exhibit the desired effectiveness as has been shown in a study carried out by Family Health International on "Contraception on Demand" (CoD) with 0.75 mg levonorgestrel. For example, in this study, a pearl index of only 18.3 could be achieved (95% confidence interval [CI] 5.0, 47.0)[3].

[3] http://f1000.com/717797870 (visited 17 Oct. 2012)

Further studies already carried out decades ago show that in various dosages postcoitally administered levonorgestrel offers contraceptive protection which is approximately comparable to the effectiveness of condoms and other barrier methods upon typical use (see e.g.: United Nations Development Programme/United Nations Population Fund/World Health Organization/World Bank Special Programme of Research, Development and Research Training in Human Reproduction; Task Force on Post-Ovulatory Methods of Fertility Regulation; "Efficacy and side effects of immediate postcoital levonorgestrel used repeatedly for contraception", Contraception 2000; 61:303-308).

Brache et al. have moreover investigated the influence of a single vaginal administration of a levonorgestrel gel directly prior to sexual intercourse on ovulation (Brache et al, Empfängnisverhütung, 2007; 76:111-116).

A vaginal application of levonorgestrel or norgestrel for on demand contraception is also proposed in WO 2010/119030 (Ulmann et al.). Therein, the active ingredients are said to be preferably administered via a vaginal ring which is used 24 hours prior to sexual intercourse. Oral, transdermal, buccal, sublingual, parenteral and rectal administration is likewise proposed therein. The dosage range claimed by Ullmann, however, is in the range of the dose used for emergency contraception (750-1500 μg LNG).

WO2007/045513 (Schering AG) describes a patch containing gestagen (inter alia levonorgestrel) and ethinylestradiol for "on demand" contraception, in which the active ingredient is administered transdermally.

Further medicament preparations for emergency contraception, as described e.g. in EP 2445491, also contain a COX inhibitor alongside the hormone, with the aim of further increasing the efficacy of the preparation.

All of the approaches described in the literature and patent literature for on demand hormonal contraception, however, failed in practice due to the fact that the described methods do not offer the contraceptive certainty which is achieved by regularly taking a hormone-containing "pill". This can be explained inter alia by the fact that the effect of the active ingredient on the inhibition of ovulation only occurs a certain time after taking the preparation, meaning that one cannot really use the term "on demand" preparation in the strict sense. One would thus in principle need to take it at least 1 to 2 days prior to sexual intercourse if a similar effectiveness to regularly taking the pill is to be achieved. However, even if this disadvantage were to be accepted, the action time of a single administration taken so early is too short, meaning that even when taken on time a pregnancy can occur since sperm can live in the cervix for up to 5 days after sexual intercourse[4]. Moreover, the required hormone dose is very high, meaning that if it is taken several times, as can arise for an "on demand" situation, the hormone load can at the very least lead to cycle disturbance in users.

[4] Weinberg C R, Wilcox A J, Biometrics 1995, 51: 405-412

It was therefore an object of the present invention to provide a method of "on demand" contraception which ensures higher contraceptive certainty compared to hormonal postcoital methods, is under the control of the woman and is taken directly prior to planned sexual intercourse (up to a maximum of 24 hours beforehand). Furthermore, higher tolerability than in the case of hormonal products for emergency contraception should be achieved by using an only reduced hormone dose.

According to the invention, this object is achieved through the use of a preparation comprising levonorgestrel and a COX inhibitor selected from the group of indomethacin, diclofenac, naproxen, ibuprofen, nimesulide, ketoprofen, piroxicam, meloxicam.

The invention is based on the surprising finding that precoital administration of the pharmaceutical composition, as disclosed in EP 2445491 A1, can achieve high contraceptive certainty and, moreover, the level of active ingredient and, more importantly, the effect on the ovary occurs after just a very short time. This was shown as described below by means of clinical data.

The invention thus relates to a method of female controlled "on demand" contraception, in which a pharmaceutical preparation comprising levonorgestrel and a COX inhibitor, selected from the group of indomethacin, diclofenac, naproxen, ibuprofen, nimesulide, ketoprofen, meloxicam, piroxicam, is administered on demand in a period of 0-24 hours prior to expected sexual intercourse.

The invention further provides the use of pharmaceutical compositions comprising levonorgestrel and a COX inhibitor selected from the group indomethacin, diclofenac, naproxen, ibuprofen, nimesulide, ketoprofen, piroxicam, meloxicam in on demand hormonal contraception ("Contraception on Demand" or for short CoD). Among the specified COX inhibitors, preference is given to indomethacin, diclofenac, naproxen, ibuprofen, nimesulide, ketoprofen or piroxicam. Particular preference is given to indomethacin, diclofenac, naproxen, ibuprofen or piroxicam.

The invention further provides an application regime for "on demand" contraception, in which an oral pharmaceutical composition comprising a COX inhibitor and levonorgestrel in a dose of 50-500 μg, preferably 100-200 μg of LNG, is taken in a period of 0-24 hours, preferably of 6-12 hours, prior to sexual intercourse, followed by a further oral pharmaceutical composition comprising 500 to 1500 μg LNG and optionally a COX inhibitor in a period of up to 48 hours after sexual intercourse.

This application regime is based on the finding that the COX inhibitor, as the clinical data demonstrate, has an effect on ovulation immediately after taking. By contrast, the levonorgestrel acts essentially only before the LH (lutinizing hormone) peak[5].

[5] Baird D T; RBMOnline—Vol. 18 Suppl. 1. 2009 32-36

By means of a corresponding application regime it is possible to achieve sufficiently high (hormone) levels in the blood plasma for a sufficiently long period to counteract an undesired pregnancy. Thus, as already explained above, sperm are viable in the female genital tract for ca. 5 days.

An even better efficacy of the preparation can thus be achieved through a corresponding application regime. The hormone load can also be further reduced in cases which have not resulted in expected sexual intercourse by dispensing with taking the second tablet, which contains the higher hormone dose.

The invention thus also provides a kit for "on demand" contraception containing 2 pharmaceutical preparations to be administered orally, in which the first preparation comprises a COX inhibitor and low dose LNG in a dose of 50-500 μg, preferably 100-200 μg, of LNG, and the second preparation comprises "high dose" LNG in a dose of 500-1500 μg, preferably 500-1000 μg, where the second preparation can optionally additionally likewise comprise a COX inhibitor. Suitable COX inhibitors are indomethacin, diclofenac, naproxen, ibuprofen, nimesulide, ketoprofen, piroxicam, meloxicam, with preference being given to indomethacin, diclofenac, naproxen, ibuprofen and piroxicam.

If it is a single-dose preparation for on demand hormonal contraception, this is used preferably in a period of 0-24, preferably 6-12, hours prior to planned sexual intercourse. Furthermore, preference is given to the taking of the single-dose preparation in a period of 0-1 h.

In an alternative embodiment, the single-dose preparation can also be taken up to at most 2 hours after sexual intercourse.

The application frequency of an "on demand" preparation should be limited to six times per cycle since more frequent application may lead to increased side effects, i.e. in particular to cycle disturbances. By contrast, for users for which an "on demand" situation arises more frequently, e.g. the use of a conventional hormonal contraceptive is recommended. In this connection, a large number of hormone-containing "pills" or other hormone-containing administration forms for contraception, such as vaginal rings (e.g. Nuvaring®) or hormone coils (e.g. Mirena®) are available.

As explained above, it is a preferred embodiment of the invention that the preparation is administered as one or two tablets. It is also possible to administer it in the form of other oral administrations such as, for example, hard capsules, orodispersible tablets, effervescent tablets or granules. Further administration forms, however, are likewise suitable for an "on demand" application. Mention is to be made here in the first instance of intravaginal rings. Such rings are already a widely established alternative to the "normal pill" in contraception. To be mentioned here in the first instance is the widely used commercial product Nuvaring®, which is described in the European patent EP 00876815 B1. The Nuvaring® is worn over a period of 3 weeks and thus offers the user contraceptive protection throughout the cycle. However, this ring is not suitable for an "on demand" application since the release kinetics of this ring are tailored to a long-term release. A rapid short-term release of active ingredient, as is required for an "on demand" situation, could not be achieved with such a ring.

A ring for an "on demand" application, which guarantees safe contraception just a short time after insertion, contains, according to the invention, as well as the hormone (levonorgestrel), also the COX inhibitor as further active ingredient. As in the case of oral application, here too different release kinetics can be achieved through a corresponding ring design, e.g. by incorporating the different active ingredients into different compartments of the ring (2-phase ring). Correspondingly designed 2-phase rings are preferred according to the invention.

The ring is inserted by the user 0-24 hours prior to planned sexual intercourse and then remains in the vagina for up to 148 hours, preferably 72 hours, after sexual intercourse.

Administering the active ingredients via a vaginal ring has the advantage over a preparation as tablet that the ring can be removed by the user if planned sexual intercourse does not occur. The hormone load of the user would thus be further reduced, especially in the case of a 2-phase ring since this releases predominantly only the COX inhibitor in the first 24 hours after insertion. A further advantage consists in being able to achieve more constant active ingredient levels over a prolonged period while avoiding very high peak plasma concentrations, as arise shortly after an oral dose, with a vaginal ring. Compared to administration via a tablet, this leads overall to a reduced systemic loading of active ingredients and thus to fewer undesired effects ("side effects").

In this method according to the invention and in the use according to the invention, "on demand" does not mean optionally. Rather, in order not to become pregnant, the woman must use the method according to the invention in every case where she can expect an undesired pregnancy.

Oral pharmaceutical preparations, as are used in the method of female controlled "on demand" contraception, comprise, if it is a single-dose preparation, levonorgestrel in an amount of 50-1500 µg, preferably 250-1500 µg. Furthermore, preference is given to an amount of leveonorgestrel of 250-500 µg.

Suitable COX inhibitors are indomethacin, diclofenac, naproxen, ibuprofen, nimesulide, ketoprofen, piroxicam, meloxicam, with preference being given to piroxicam, naproxen, ibuprofen, diclofenac and indomethacin.

The amount of COX inhibitor present in the pharmaceutical preparation varies depending on the inhibitor chosen.

According to the invention, the following dose ranges are suitable for an "on demand" application:
Indomethacin: 50-400 mg/day[6]
Diclofenac: 50-400 mg/day
Naproxen: 500-3000 mg/day
Ibuprofen: 500-5000 mg/day
Nimesulide: 100-500 mg/day
Ketoprofen: 100-500 mg/day
Piroxicam: 10-80 mg/day
Meloxicam: 5-60 mg/day

[6] If it is a single-dose tablet, the stated amount corresponds to the amount of COX inhibitor contained in the tablet If the oral pharmaceutical preparation, as is used in the method for female controlled "on demand" contraception, consists of 2 tablets, the first tablet contains besides one of the aforementioned COX inhibitors in the stated dose ranges also low dose LNG in a dose of 50-500 µg, preferably 100-200 µg LNG, and the second tablet contains "high dose" LNG in a dose of 500-1500 µg, preferably 500-1000 µg LNG, where the second tablet can optionally additionally likewise contain a COX inhibitor.

Corresponding preparations containing LNG and a COX inhibitor can be prepared, as disclosed in EP 2445491 A1, by combining the active ingredients with the customary pharmaceutical auxiliaries and then pressing them to give a tablet. Further preparation options are disclosed in Examples 3-5 of the present application.

The invention is illustrated in more detail below by reference to working examples. These working examples serve merely as an explanation, and in no way have a limiting effect on the protected subject matter of the present invention.

EXAMPLE 1

Influence of a Single Dose of Piroxicam on the Ovulation of Women

In a clinical phase IIa study (monocentric, double blind, placebo controlled, randomized, parallel groups), piroxicam was administered to women of a fertile age in the dosages 20, 40 and 80 mg as an oral single dose. Overall, 72 women were treated, of which 18 women were given 20 mg, 17 women were given 40 mg, 20 women were given 80 mg of piroxicam and 17 women were given a placebo preparation. It was the aim of the study to investigate whether the oral single administration of piroxicam after the start of the LH increase has an effect on ovulation compared to the placebo in healthy young women. An ovulation inhibition or delay by at least plus 24 hours longer than the median duration between LH increase and ovulation in the untreated previous cycle of the study population was evaluated as the effect. For this purpose, transvaginal ultrasound investigations and hormone level measurements were carried out. Only women (n=64) without serious protocol deviations which could have influenced the study aim were included in the final study evaluation.

It was shown that an ovulation inhibition and/or delay resulted in all treatment groups. In the placebo group, 2 women showed an ovulation delay of at least plus 24 hours compared to the untreated previous cycle. An ovulation inhibition or delay of at least plus 24 hours was demonstrated in the 20 mg group for 8 women, in the 40 mg group for 7 women and in the 80 mg group for 11 women. The result of this study shows in all three piroxicam dose groups a more marked effect on ovulation than in the placebo group.

The greatest response rate was seen in the highest piroxicam dosage (80 mg) (see Table 1; FIG. 1/1).

TABLE 1.1

Number of women who exhibited an at least plus 24 hour delay in ovulation compared to the median time between LH increase and ovulation in the untreated previous cycle; final evaluation set

|  | Placebo N = 16 | 20 mg Piroxicam N = 16 | 40 mg Piroxicam N = 16 | 80 mg Piroxicam N = 16 |
|---|---|---|---|---|
| Number (%) of women | 2 (12.5%) | 8 (50.0%) | 7 (43.8%) | 11 (68.8%) |

Furthermore, it can be seen that as the dose of piroxicam increases, the time (median) between LH increase and ovulation in the treatment cycle is extended compared to the previous cycle: placebo—3 hours; 20 mg piroxicam—17 hours; 40 mg piroxicam—15 hours and 80 mg piroxicam—228 hours (see Table 1.2 and FIG. 1/1).

TABLE 1.2

Time [hours] from LH increase to ovulation per cycle; final evaluation set

|  |  | Placebo N = 16 | 20 mg Piroxicam N = 16 | 40 mg Piroxicam N = 16 | 80 mg Piroxicam N = 16 |
|---|---|---|---|---|---|
| Time [hours] from LH increase to ovulation in the previous cycle | Average value | 47 | 48 | 44 | 58 |
|  | Median | 47 | 47 | 47 | 49 |
|  | Range | 35-58 | 33-72 | 24-58 | 32-96 |
| Time [hours] from LH increase to ovulation in the treatment cycle | Average value | 55 | 133 | 121 | 219 |
|  | Median | 50 | 65 | 63 | 276 |
|  | Range | 33-72 | 38-416 | 37-384 | 48-386 |

EXAMPLE 2

Influence of the Single Applications of Levonorgestrel and COX Inhibitors Alone or in Combination on the Fertility of Rats To demonstrate the effect of substances on fertility, the rat is a particularly suitable animal model since the cycle can be easily observed using vaginal smears and a pairing reliably generates a large number of offspring.

In the experiments below, female Han Wistar rats with a weight of 200-270 g were used. The animals were kept in Macrolon cages in rooms with controlled lighting (12 hours darkness: 12 hours lightness), fed with a standard diet and watered with water ad libitum.

Levonorgestrel was dissolved in benzyl benzoate/castor oil (1+4 v/v) and the daily dose was applied in a volume of 1 ml/kg of body weight s.c.

The COX inhibitors were suspended in a carrier liquid (85 mg Myrj®53 polyoxyl(50)stearate; CAS No. 9004-99-3) in 100 ml of 0.9% w/v NaCl solution) and the dose corresponding to the treatment group was administered orally in a volume of 2 ml/kg of body weight.

Two cycles were observed using vaginal smears prior to the start of the experiment. Only animals with a regular 4-day cycle were included in the experiment. Assignment to the treatment groups was random.

The animals were treated once with the test substances either on their own or in combination in pro oestrus, the day in the cycle on which in the evening the LH peaked. On the evening of pre oestrus the female animals were paired with male rats. Successful pairing was tested the next morning by means of a vaginal sperm detection in the vaginal smear. The influence on the fertility was ascertained 9-15 days after the pairing via the number of implantation sites of the animals. The group size was n=6 animals per group.

As is evident from Tables 2.1 and 2.2, in these experiments piroxicam and indomethacin in combination with levonorgestrel exhibited a strong antifertile effect, whereas the individual doses had no effect or only a considerably lower effect. In the experiments with diclofenac and ibuprofen, the combinations with levonorgestrel likewise exhibited the strongest effect in each case compared to the application of the respective individual substances (Tables 2.3 and 2.4).

TABLE 2.1

Influence of a single application of levonorgestrel (LNG) or piroxicam on their own or in combination on the fertility of female rats.

| Treatment group | Time of treatment (time of day) | Sum of the implantation site, of 6 animals | Implantations per animal (average value ± SD) |
|---|---|---|---|
| Vehicle | 7:00 | 77 | 12.8 ± 1.8 |
| LNG 0.5 mg/animal | 7:00 | 50 | 8.3 ± 4.3 |
| Piroxicam 2 mg/animal | 7:00 | 57 | 9.5 ± 4.8 |
| LNG 0.5 mg/animal + Piroxicam 2 mg/animal | 7:00 | 10 | 1.7 ± 2.1 |
| LNG 0.5 mg/animal | 13:00 | 32 | 5.3 ± 3.1 |
| Piroxicam 2 mg/animal | 13:00 | 60 | 10.0 ± 5.3 |
| LNG 0.5 mg/animal + Piroxicam 2 mg/animal | 13:00 | 14 | 2.3 ± 1.2 |

TABLE 2.2

Influence of a single application of levonorgestrel (LNG) or indomethacin on their own or in combination on the fertility of female rats.

| Treatment group | Time of treatment (time of day) | Sum of the implantation sites of 6 animals | Implantations per animal (average value ± SD) |
|---|---|---|---|
| Vehicle | 17:00 | 65 | 10.8 ± 5.5 |
| LNG 0.5 mg/animal | 17:00 | 45 | 7.5 ± 4.0 |
| Indomethacin 1 mg/animal | 17:00 | 29 | 4.8 ± 4.1 |
| LNG 0.5 mg/animal + Indomethacin 1 mg/animal | 17:00 | 12* | 2.4 ± 3.7* |

*Data from n = 5 animals since one animal was not paired (no sperm detection in the vaginal smear)

TABLE 2.3

Influence of a single application of levonorgestrel (LNG) or diclofenac on their own or in combination on the fertility of female rats.

| Treatment group | Time of treatment (time of day) | Sum of the implantation sites of 6 animals | Implantations per animal (average value ± SD) |
|---|---|---|---|
| Vehicle | 17:00 | 78 | 13.0 ± 1.1 |
| LNG 0.5 mg/animal | 17:00 | 34* | 6.8 ± 5.9* |
| Diclofenac 4 mg/animal | 17:00 | 22 | 3.7 ± 3.6 |
| LNG 0.5 mg/animal + Diclofenac 4 mg/animal | 17:00 | 18 | 3.0 ± 3.0 |

*Data from n = 5 animals since one animal was not paired (no sperm detection in the vaginal smear)

TABLE 2.4

Influence of a single application of levonorgestrel (LNG) or ibuprofen on their own or in combination on the fertility of female rats.

| Treatment group | Time of treatment (time of day) | Sum of the implantation sites of 6 animals | Implantations per animal (average value ± SD) |
|---|---|---|---|
| Vehicle | 17:00 | 76 | 12.7 ± 2.0 |
| LNG 0.5 mg/animal | 17:00 | 63 | 10.5 ± 4.5 |
| Ibuprofen 12.5 mg/animal | 17:00 | 65 | 10.8 ± 3.2 |
| Ibuprofen 25 mg/animal | 17:00 | 68 | 11.3 ± 2.6 |
| LNG 0.5 mg/animal + Ibuprofen 12.5 mg/animal | 17:00 | 27 | 4.5 ± 3.9 |
| LNG 0.5 mg/animal + Ibuprofen 25 mg/animal | 17:00 | 47 | 7.8 ± 3.4 |

TABLE 2.5

Influence of a single application of levonorgestrel (LNG) or naproxen on their own or in combination on the fertility of female rats.

| Treatment group | Time of treatment (time of day) | Sum of the implantation sites of 6 animals | Implantations per animal (average value ± SD) |
|---|---|---|---|
| Vehicle | 17:00 | 78 | 13.0 ± 1.9 |
| | 20:00 | | |
| LNG 0.5 mg/animal | 17:00 | 39* | 7.8 ± 5.9 |
| Naproxen 10 mg/animal | 20:00 | 23** | 5.8 ± 4.4 |
| Naproxen 2 × 5 mg/animal | 17:00 | 44 | 7.3 ± 3.6 |
| | 20:00 | | |
| LNG 0.5 mg/animal + naproxen 10 mg/animal | 17:00 | 44 | 8.8 ± 2.1 |
| LNG 0.5 mg/animal + naproxen 2 × 5 mg/animal | 17:00 | 43 | 7.2 ± 3.0 |
| | 20:00 | | |

*Data from n = 5 animals since one animal died during pregnancy
**Data from n = 4 animals since two animals died during pregnancy The administration of 10 mg/animal naproxen on its own brought about a reduction in fertility in rats (see Table 2.5). However, the combination of naproxen and levonorgestrel did not lead to a further-reaching reduction in implantation sites in the rat fertility test. However, it could be shown that the prostaglandin E2 (PEG2) synthesis in the ovaries was reduced under the action of naproxen, although the increase in the PEG2 concentration in the ovaries before ovulation was not completely inhibited (see Table 2.6). The incomplete inhibition of the increase in PEG2 concentration in the ovaries probably led to the administration of naproxen not intensifying the antifertile effect of levonorgestrel in the rat fertility model. However, for technical reasons (solubility of naproxen, no further applications during the pairing process), a higher dose of naproxen which would have led to complete inhibition of the PEG2 synthesis in the ovaries cannot be tested in this rat model. Smith et al. observed that the taking of naproxen over a prolonged period for treating Bechterew's disease had an antifertile effect [Smith et al. Br J Rheumatol. 1996; 35(5):458-62]. These observations show that naproxen inhibits fertility in humans. However, they give no indication whether the single administration of naproxen in combination with a gestagen prior to sexual intercourse already has an antifertile effect. On account of the demonstrated inhibition of the PEG2 synthesis in the ovaries, however, it must be assumed that naproxen, after a single dose, has the same effect as piroxicam, indomethacin, diclofenac and ibuprofen on ovulation.

Furthermore, it was able to be shown that the administration of naproxen strongly inhibits the PEG2 synthesis in plasma (see Table 2.6). Jonsson and Hammarström were able to show in a clinical study that the administration of a prostaglandin synthesis inhibitor (diclofenac), led to a reduction in cervical secretion [Jonsson and Hammarström. Human Reproduction 1993; 8(8)1168-1172]. Furthermore, it is known that the prostaglandin concentrations in cervical mucous at the time of ovulation are very high and have a positive influence on the migration of the sperm in the cervical mucous [Charbonnel et al. Fertility and Sterility 1982; 38:109-111; Eskin et al. Obstet Gynecol. 1973 March; 41(3):436-9]. Consequently, the inhibition of the PEG2 synthesis in the plasma by the administration of naproxen could have an effect on the cervical mucous and enhance the antifertile effect of gestagens on the cervical mucous.

Since the data demonstrate an inhibition of the PEG2 synthesis by the administration of naproxen, the method for female controlled "on demand" contraception, characterized in that a pharmaceutical preparation comprising levonorgestrel and naproxen is administered on demand and once in a period of 0-24 hours prior to expected sexual intercourse, is provided by the invention.

TABLE 2.6

PEG2 concentration [pg/500 μg tissue] in the ovaries 2, 4 and 6 hours following oral application of 20 mg/kg naproxen (administration was carried out around 16:00 hours).

| | Prostaglandin E2 in the ovaries [pg/500 μg tissue] | | | | Prostaglandin E2 in the plasma [pg/500 μg tissue] | | | |
|---|---|---|---|---|---|---|---|---|
| Time of taking the sample (time of day) | Vehicle Average value | SE | Naproxen Average value | SE | Vehicle Average value | SE | Naproxen Average value | SE |
| 18:00 | 60.8 | 16.8 | 12.9 | 0.9 | 120.7 | 65.0 | 21.5 | 3.5 |
| 20:00 | 141.7 | 85.7 | 32.1 | 10.3 | 100.6 | 21.0 | 23.3 | 7.8 |
| 22:00 | 290.5 | 139.2 | 72.4 | 19.0 | 184.0 | 63.1 | 20.5 | 4.4 |

EXAMPLE 2a

Influence of the Single Applications of Levonorgestrel and COX Inhibitors Alone or in Combination on the Fertility of Rats—Influence on the Cervical Mucous The cervical mucous plays an important role in contraception since, depending on the cycle, it favours or prevents sperm from migrating from the vagina into the uterus. On the days around ovulation, the otherwise viscous cervical mucous becomes thin, glass-clear and thread-drawing under the effect of the oestrogen formed at this time. The characteristic formation of fern-like NaCl crystals in the dried cervical mucous occurs (ferning). This structure allows the sperm to climb into the uterus. On nonfertile days, the cervical mucous loses this property under the influence of progesterone and is viscous to sticky, of pasty consistency and serves as a natural barrier to seal the opening of the uterus. Consequently, on nonfertile days, the cervical mucous prevents sperm from migrating into the uterus. The prevention of conception of gestagen-containing contraceptives is based inter alia also on the effect of the gestagens on the cervical mucous.

The effect of the gestagens on the cervical mucous is important for on demand contraception compared to emergency contraception since it makes a significant contribution to the effectiveness of the gestagens in the case of on demand contraception. In the case of emergency contraception, the effect of the gestagens on the cervical mucous plays no role since the contraception is used several hours after sexual intercourse and the sperm have consequently already migrated into the uterus at the time of taking. The influence of pharmacological contraceptives on the cervical mucous is investigated with the help of the sperm migration test (sperm swim-up analyses) and with the analysis of the influence on the formation of the fern-like NaCl crystals in the dried cervical mucous (ferning).

EXAMPLE 3

Combination Tablets containing 60 mg of Piroxicam and 0.5 mg of Levonorgestrel A fluidized-bed granulator is charged with 4.17 g of levonorgestrel, 500 g of piroxicam, in each case 422.9 g of lactose monohydrate and microcrystalline cellulose, and 60 g of croscarmellose sodium. This powder mixture is granulated with a granulating liquid which consists of 60 g of hydroxypropylmethylcellulose 5 cP, 15 g of sodium laurylsulphate and 1440 g of water. After drying the granules in the fluidized-bed granulator and subsequent sieving, the granules are after-mixed with 15 g of magnesium stearate for 5 minutes. The powder mixture is then pressed on a rotary tabletting press to give round tablets with a mass of 180 mg and a diameter of 8 mm. The tablets are then coated with a dispersion of 44.2 g of a finished-film coating powder and 250.3 g of water. The finished-film coating powder consists to 50.56% of Hypromellose 5 cP, 10.12% Macrogol 3350, 10.12% talc, 23.20% titanium dioxide and 6.00% iron oxide. The tablets have to be taken by the woman 6-12 hours before planned sexual intercourse.

EXAMPLE 4

Kit containing 100 mg of Diclofenac and 1 mg of Levonorgestrel

A folded box is manufactured which contains diclofenac slow-release capsules 100 mg and levonorgestrel tablets 1 mg. Furthermore, the folded box contains a pack insert which describes that the diclofenac slow-release capsules are to be taken orally by the woman 6 to 12 hours prior to sexual intercourse and the levonorgestrel tablets are to be taken within 24 hours afterwards. Furthermore, the pack insert points out that the taking of the levonorgestrel tablets can be dispensed with if sexual intercourse does not occur.

The diclofenac slow-release capsules 100 mg are produced as described in EP 0519870B1.

To produce the levonorgestrel tablets 1 mg, a fluidized-bed granulator is charged with 17.6 g of levonorgestrel, 907 g of lactose, 459 g of microcrystalline cellulose and 45 g of croscarmellose sodium. The powder mixture is granulated with a granulating liquid made of 60 g of hydroxypropyl-methylcellulose 5 cP and 1440 g of water. After drying and sieving, the product is after mixed with 12 g of magnesium stearate and pressed to give round tablets with a mass of 85 mg and a diameter of 6 mm on a rotary tabletting press. The tablets are coated with 35.3 g of finished-film coating powder which has the same composition as given in Example 2. The diclofenac slow-release capsules and the levonorgestrel tablets are sealed into two blister cavities of a blister strip, the blister is strips also having printed thereon instructions that the capsule is to be taken before sexual intercourse and the tablet is to be taken after sexual intercourse whenever necessary.

EXAMPLE 5

Orodispersible Tablets containing 75 mg of Indomethacin and 0.25 mg of Levonorgestrel An auxiliary mixture consisting of mannitol, sorbitol, polyplasdone XL and syloid is prepared as described in WO2003051338 Example 1 formulation A. Subsequently, a premix of 31.3 g of levonorgestrel and 0.282 kg of the above auxiliary mixture is prepared. The premix is mixed with 9.38 kg of indomethacin, 31.1 kg of the above auxiliary mixture and 638 g of peppermint aroma. A further 1.06 kg of magnesium stearate is added and the mixture is remixed. This compression-ready mixture is pressed on a rotary tabletting press to give orodispersible tablets (orally disintegrating tablets) with a mass of 340 mg and a diameter of 10 mm. In each case two orodispersible tablets are sealed into an Alu/Alu blister and packaged into a folding box together with a pack insert. The pack insert contains instructions that one orodispersible tablet should be taken at the latest 6 hours before planned sexual intercourse and a further orodispersible tablet should be taken within 24 hours after sexual intercourse has taken place. If no sexual intercourse has occurred, the taking of the second orodispersible tablet can be dispensed with. Furthermore, the pack insert describes that the tablets are to be taken without water by placing them in the mouth. The tablets disintegrate on the tongue and the resulting dispersion is swallowed.

DESCRIPTION OF THE FIGURES

FIG. 1/1

Adapted Kaplan-Meier curve for depicting the ovulation delay following administration of piroxicam compared to the administration of a placebo preparation. The depiction is based on the values shown in Table 1.2. The time after the LH increase is plotted on the X axis in days. The Y axis shows the number of investigated women in which no ovulation has taken place [%]. The individual curves represent the individual treatment groups: placebo group (solid line); 20 mg of piroxicam (dotted line consisting of short strokes), 40 mg of piroxicam (dotted line consisting of long strokes) and 80 mg of piroxicam (dotted line consisting of alternating long and short strokes).

The invention claimed is:

1. A method of female controlled "on demand" contraception, comprising administering a pharmaceutical composition comprising levonorgestrel and a COX inhibitor, selected from the group consisting of indomethacin, diclofenac, and piroxicam, to a female on demand and once in a period of 0-24 hours prior to expected sexual intercourse.

2. The method according to claim 1, characterized in that the pharmaceutical formulation is administered once 0-6 hours prior to expected sexual intercourse.

3. The method according to claim 1, characterized in that the pharmaceutical formulation is administered once 0-1 hours prior to expected sexual intercourse.

4. The method of claim 1, characterized in that the COX inhibitor is diclofenac.

5. The method of claim 1, characterized in that the COX inhibitor is indomethacin.

6. The method of claim 1, wherein the amount of COX inhibitor administered is selected from the group consisting of
Indomethacin: 50-400 mg/day;
Diclofenac: 50-400 mg/day; and
Piroxicam: 10-80 mg/day.

7. The method of claim 1, wherein 50-1500 µg of levonorgestrel is administered.

8. The method of claim 1, wherein 250-1500 µg of levonorgestrel is administered.

9. The method of claim 1, wherein 250-500 µg of levonorgestrel is administered.

10. A method of hormonal female controlled "on demand" contraception, comprising in a period of 0-24 hours prior to expected sexual intercourse taking a ft rst pharmaceutical composition, and in a period of 0-48 hours after sexual intercourse taking a second pharmaceutical composition, where the preparations taken before and after sexual intercourse are identical and comprise (a) a COX inhibitor selected from the group of indomethacin, diclofenac, and piroxicam, and (b) levonorgestrel.

11. A method of hormonal female controlled "on demand" contraception, comprising in a period of 0-24 hours prior to expected sexual intercourse taking a first pharmaceutical composition, and in a period of 0-48 hours after sexual intercourse taking a second pharmaceutical preparation is taken, where the first pharmaceutical composition comprises (a) a COX inhibitor selected from the group of indomethacin, diclofenac, and piroxicam and (b) levonorgestrel in a dose of 50-500 µg, and the second pharmaceutical composition comprises levonorgestrel in a dose of 500-1500 µg and optionally the COX inhibitor selected in the first pharmaceutical composition.

12. A method of hormonal female controlled "on demand" contraception, characterized in that a vaginal ring containing levonorgestrel and a COX inhibitor, selected from the group of indomethacin, diclofenac, piroxicam, is used in a period of 0-24 hours prior to expected sexual intercourse and is worn up to 148 hours after sexual intercourse.

13. An application regime for hormonal female controlled "on demand" contraception, characterized in that a pharmaceutical composition comprising levonorgestrel and a COX inhibitor, selected from the group of indomethacin, diclofenac, and piroxicam, is taken in a period of 0-24 hours prior to expected sexual intercourse and in a period of 0-48 hours after sexual intercourse.

14. The application regime according to claim 13, characterized in that the first tablet taken prior to sexual intercourse comprises (a) a COX inhibitor selected from the group of indomethacin, diclofenac, and piroxicam and (b) levonorgestrel in a dose of 50-500 µg, and the second tablet taken after sexual intercourse comprises levonorgestrel in a dose of 500-1500 µg and optionally in addition the COX inhibitor selected in each case in the first tablet.

15. Application regime according to claim 13, characterized in that the first tablet taken prior to sexual intercourse comprises, as COX inhibitor,
Indomethacin: 50-400 mg/day;
Diclofenac: 50-400 mg/day; and
Piroxicam: 10-80 mg/day
in the specified dose.

16. A kit for use in the method of hormonal female controlled "on demand" contraception according to claim 10, comprising a first tablet to be taken before sexual intercourse and a second tablet to be taken after sexual intercourse, characterized in that both tablets contain both a COX inhibitor selected from the group of indomethacin diclofenac and piroxicam.

17. A kit for use in the method for hormonal female controlled "on demand" contraception according to claim 11, comprising a first tablet to be taken prior to sexual intercourse and a second tablet for taking after sexual intercourse, characterized in that the first tablet comprises a COX inhibitor selected from the group of indomethacin, diclofenac, piroxicam and levonorgestrel in a dose of 50-500 µg, and the second tablet comprises levonorgestrel in a dose of 500-1500 µg and optionally with the COX inhibitor selected in each case in the first tablet.

\* \* \* \* \*